United States Patent [19]
Vought

[11] Patent Number: 5,853,363
[45] Date of Patent: Dec. 29, 1998

[54] SURGICAL MICROSCOPE OPERATING DRAPE AND METHODS OF OPERATION AND MANUFACTURE THEREOF

[75] Inventor: Kimber L. Vought, Columbus, Miss.

[73] Assignee: Deka Medical, Inc., Columbus, Mich.

[21] Appl. No.: 901,510

[22] Filed: Jul. 28, 1997

[51] Int. Cl.[6] .................................................. A61B 1/04
[52] U.S. Cl. .................... 600/121; 600/122; 359/510; 359/511; 128/849
[58] Field of Search ................................ 600/121, 122, 600/124, 125; 359/510, 511, 513; 206/316.1, 316.2, 316.3, 363, 438; 128/849, 850, 851

[56] References Cited

U.S. PATENT DOCUMENTS

| | | | |
|---|---|---|---|
| 3,528,720 | 9/1970 | Treace | 359/510 |
| 3,698,791 | 10/1972 | Walchle et al. | 359/510 |
| 4,183,613 | 1/1980 | Walchle et al. | 359/510 |
| 4,266,663 | 5/1981 | Geraci | 359/510 |
| 4,561,540 | 12/1985 | Hunter et al. | 359/510 X |
| 4,799,779 | 1/1989 | Mesmer | 359/510 |
| 5,155,624 | 10/1992 | Flagler | 359/510 |
| 5,274,500 | 12/1993 | Dunn | 359/510 X |
| 5,311,358 | 5/1994 | Pederson et al. | 359/510 |
| 5,608,574 | 3/1997 | Heinrich | 359/510 |

OTHER PUBLICATIONS

Advertisement and Instructions for "Opmi Drape—sterile disposable drapes" by Carl Zeiss, Inc.; pp. 1–8 Product No. 99 60 48.

Advertisement for "Universal Microscope Drape" by Microtek Medical; 2 pages Product No. 6920.

Advertisement for "Microscope Drapes" by Microtek Medical; 5 pages.

Advertisement for "Microscope Drapes" by Richards (Microdrape® I, and Microdrape® II) 6 pages.

*Primary Examiner*—Beverly M. Flanagan

[57] ABSTRACT

For use with a surgical microscope having an objective lens barrel protruding therefrom, drapes, methods of draping the microscope and methods of manufacturing the drapes. In one embodiment, a drape includes: (1) a sheet, having an elastically-deformable objective lens aperture therethrough, that covers at least a portion of the surgical microscope, the objective lens aperture adapted to receive the objective lens barrel therethrough and elastically constrict about the objective lens barrel and (2) a transparent objective lens cover, separate from the sheet and having a flexible barrel adapter, the flexible barrel adapter expandable to fit about and cover the objective lens barrel, the sheet and the objective lens cover cooperating to cover the portion of the surgical microscope, including the objective lens barrel.

21 Claims, 2 Drawing Sheets

2

SURGICAL MICROSCOPE OPERATING DRAPE AND METHODS OF OPERATION AND MANUFACTURE THEREOF

TECHNICAL FIELD OF THE INVENTION

The present invention is directed, in general, to surgical drapes and, more specifically, to a surgical microscope operating drape and methods of draping a surgical microscope and manufacturing the drape.

BACKGROUND OF THE INVENTION

A surgical field, as found in a typical hospital's operating room, is an environmentally controlled area where the risk of infection from naturally occurring organisms is minimized. The environment's cleaniless is controlled by limiting the introduction of infection creating organisms and other contaminants by maintaining strict controls over the personnel and equipment that are present in the surgical field.

One way to minimize the risk of infection to surgical patients in the operating room is with the use of equipment and personnel drapes. The drapes are placed over the patient, operating room staff and/or equipment to form a sterile barrier, keeping any organisms and contaminants that may cause infections from migrating to exposed tissue and open wounds. Also, the drapes prevent the fluids, such as blood, that are produced during most surgical procedures from settling on the operating room's furniture and equipment. These fluids are splattered when, for instance, a vein or artery is severed. The splattered fluids will ultimately settle on the drapes and not on draped furniture and equipment.

The advancement of medical procedures has correspondingly increased the need of more advanced medical equipment. The surgical microscope has become an integral part of the operating room. Currently, as surgical procedures are becoming increasingly more complex, the surgical microscope has allowed the surgeon unprecedented observation of the region under operation. This has allowed more complex procedures to be attempted with an increased probability of patient recovery.

The surgical microscope is typically a ceiling-mounted device that may be raised or lowered and positioned over any part of the patient's body. The surgical microscope often has multiple eyepieces that permit the surgeon others simultaneously to view the magnified area under the microscope's objective lens.

A microscope drape, used to create a sterile barrier, is often initially affixed to the microscope at the lens housing for the objective lens, to orient the drape with respect to the remaining structure of the microscope. Once the microscope drape is attached to the objective lens barrel, other portions of the drape may be spread and positioned to cover the remainder of the microscope structure.

The objective lens barrels for comparable microscopes of different manufacturers are often of different sizes. Thus, a microscope drape that fits the objective lens barrel of one microscope may not fit the objective lens barrel of a similar microscope made by a different manufacturer. Consequently, larger and more expensive inventory of several different drapes is necessary to accommodate the different microscope objective lens barrels. Furthermore, several surgical microscopes have objective lens barrels that are close in size. Accordingly, if an incorrect drape is used and the fit is not secured, sudden slippage of the mounting device, such as a mounting ring, into the surgical field could occur during an operation, resulting in serious complications to the patient.

Therefore, what is needed in the art is a more flexible, lower cost alternative to such prior art single-piece surgical microscope operating drapes. Further, what is needed in the art are improved methods of draping a surgical microscope and methods of manufacturing a surgical microscope operating drape.

SUMMARY OF THE INVENTION

To address the above-discussed deficiencies of the prior art, it is a primary object of the present invention to provide a more universal microscope drape.

In the attainment of the above-described primary object, the present invention provides, for use with a surgical microscope having an objective lens barrel protruding therefrom, drapes, methods of draping the microscope and methods of manufacturing the drapes. In one embodiment, a drape includes: (1) a sheet, having an elastically-deformable objective lens aperture therethrough, that covers at least a portion of the surgical microscope, the objective lens aperture adapted to receive the objective lens barrel therethrough and elastically constrict about the objective lens barrel and (2) a transparent objective lens cover, separate from the sheet and having a flexible barrel adapter, the flexible barrel adapter expandable to fit about and cover the objective lens barrel. The sheet and the objective lens cover cooperate to cover the portion of the surgical microscope, including the objective lens barrel.

The present invention therefore introduces a two-piece surgical microscope operating drape having features that allow the sheet and the objective lens cover to be more flexible in the types of microscopes that they can accommodate. Because they are wholly separate, relatively few sheets and objective lens covers may be combined to fit a wide range of microscopes, thereby avoiding the significant expense of the prior art drapes discussed above. For purposes of the present invention, "sheet" is defined broadly to include not only sheets in planar form, but also in cylindrical or tubular form (irrespective of whether the ends of the cylinder or tube are open or closed). "Sheet" is further defined to include extrudable materials (such as plastic) as well as woven materials (such as cloth).

In one embodiment of the present invention, the objective lens aperture has an elastic band thereabout to render the objective lens cover elastically deformable. In an embodiment to be illustrated and described, the elastic band is bonded (perhaps by gluing or sewing) to the sheet and extends entirely about the objective lens aperture. This need not be the case, however.

In one embodiment of the present invention, the objective lens aperture forms a particle-resistant seal about the objective lens barrel. A particle-resistant seal, while advantageously protecting the microscope against contamination, is not necessary to the present invention.

In one embodiment of the present invention, the objective lens cover is composed in part of plastic. Alternatively, the objective lens cover may be composed of another transparent material, such as glass or quartz.

In one embodiment of the present invention, the flexible barrel adapter comprises a resilient gasket. The resilient gasket expands to the extent necessary to allow the objective lens barrel to be inserted into the objective lens cover. Those skilled in the art will perceive other means by which the barrel adapter may be made flexible without requiring a flexible gasket.

In one embodiment of the present invention, the flexible barrel adapter fits over the sheet proximate the objective lens aperture. Alternatively, the flexible barrel adapter may simply abut the sheet or allow a portion of the objective lens barrel to be exposed.

In one embodiment of the present invention, the drape further comprises at least one hook-and-pile fastener (commonly known as Velcro®, manufactured by the DuPont Corporation), coupled to the sheet, that fixes the sheet to the portion of the surgical microscope. Those skilled in the art are familiar with many acceptable ways to fix a drape to a microscope apart from a hook-and-pile fastener.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
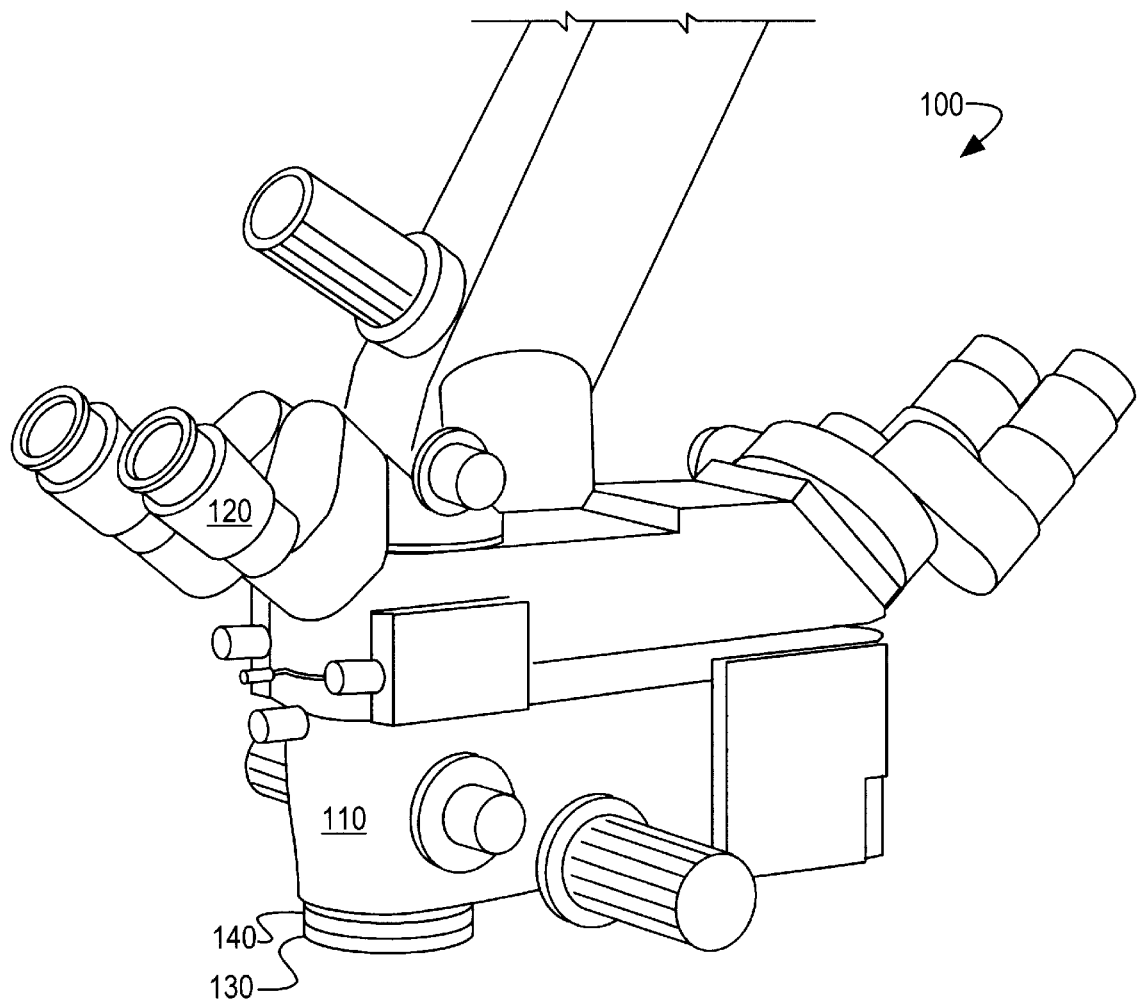
FIG. 1 illustrates an exemplary surgical operating microscope.

Referring initially to FIG. 1, illustrated is an exemplary surgical operating microscope 100. The surgical operating microscope 100 has a main body 110 with a plurality of eyepieces (one of which is designated 120) extending upwardly from the main body 110. Also shown is an objective lens 130 coupled to an objective lens barrel 140. The objective lens barrel 140 projects downwardly from the main body 110 such that, when the microscope 100 is placed over the patient's body, the objective lens 130 points down toward the body. The eyepieces 120 provide the surgeon and/or other surgical team members visual control in a precise fashion over the patient through the objective lens 130.

Figure 2:
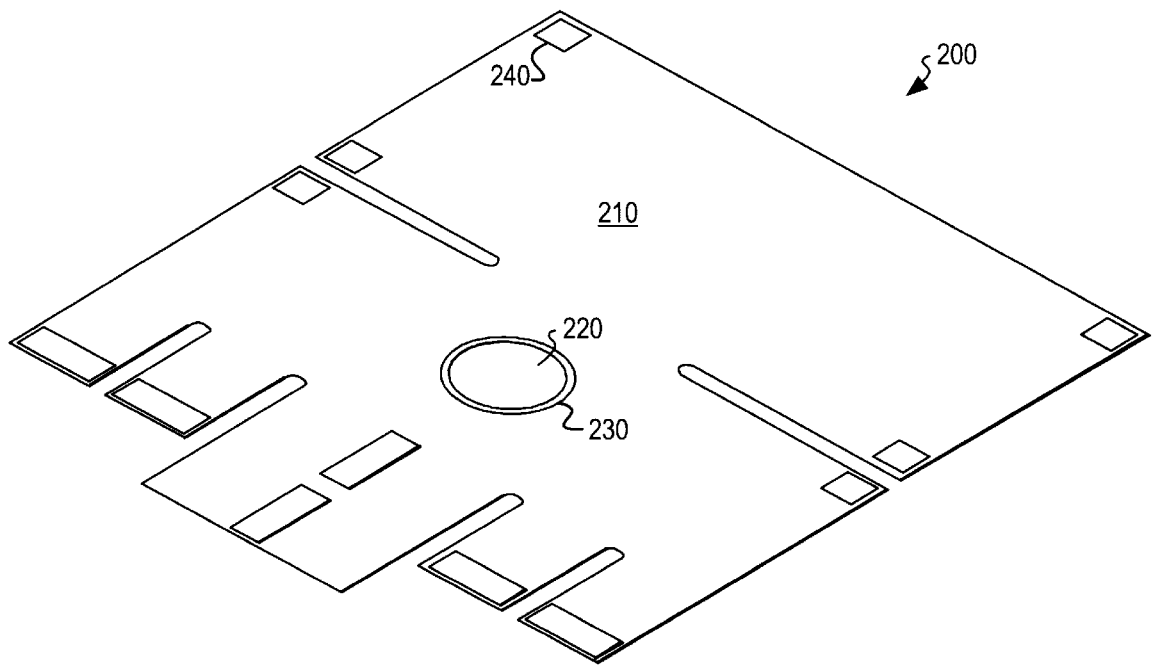
FIG. 2 illustrates an embodiment of a microscope drape constructed according to the principles of the present invention.

Turning now to FIG. 2, illustrated is an embodiment of a microscope drape 200 constructed according to the principles of the present invention. The microscope drape 200 includes a sheet 210, which, in a preferred embodiment, is formed as a tube having a single closed end, that has an objective lens aperture 220 opening through the sheet 210. Also shown is a constricting band 230 surrounding the objective lens aperture 220. A plurality of fasteners (one of which is designated 240) are shown attached to both ends of the sheet 210.

The sheet 210 (again, preferably in the form of a tube) has dimensions that allow the sheet 210 substantially to cover the surgical operating microscope main body 110. Those skilled in the art are aware that surgical operating microscopes 100 vary in size and dimensions and that the dimensions of the sheet 210 are selected to accommodate the largest microscope 100 dimensions in use. The materials that may be used for the sheet 210, as those skilled in the art are aware, are typically those materials that are suitable for use in the operating room environment, e.g., a heat-resistant polymer. The constricting band 230 that surrounds the objective lens aperture 220 in a preferred embodiment is an elastic band (sewn or otherwise secured to the sheet 210 about a periphery of the objective lens aperture 220), allowing the objective lens aperture 220 to accommodate objective lens barrels 140 with varying diameters. The diameter of the resulting aperture 220 is preferably smaller than the smallest diameter objective lens barrel 140 that is commonly in use when fully constricted and slightly larger than the largest diameter objective lens barrel 140 that is commonly in use when fully stretched. In another embodiment, the constricting band 230 forms a particle-resistant seal when stretched over the objective lens barrel 140. The particle-resistant seal keeps particles from passing between the constricting band 230 and the objective lens barrel 140 and contaminating the main body 110 of the microscope 100.

The sheet 210 is dressed onto the microscope 100 by stretching and securing the elasticated material of the constricting band 230 around the objective lens barrel 140 to form a seal. The sheet 210 is then wrapped around the microscope 100 body with the eyepieces 120 exposed and secured with the fasteners 240. The fasteners 240 in the illustrated embodiment are hook-and-pile fasteners (widely known as Velcro®, one brand name under which such fasteners are commercially available), however, other fastening methods and devices are well known in the art, such as ties or safety pins.

Figure 3:
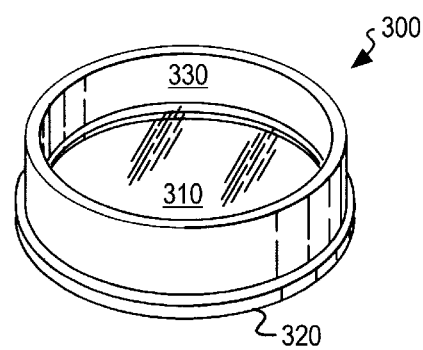
FIG. 3 illustrates an embodiment of a microscope objective lens cover.

Turning now to FIG. 3, illustrated is an embodiment of a microscope objective lens cover 300. The microscope objective lens cover 300 includes an outer cover 310, an outer cover frame 320 and a flexible barrel adapter 330 that provide a protective cover for the objective lens 130 from fluids and contaminants usually encountered during a surgical procedure. The outer cover 310 and outer cover frame 320 may be composed of plastic or any other transparent material, such as glass. Alternatively, the outer cover 310 and the outer cover frame 320 may be composed of a combination of materials, such as glass and plastic, respectively. In another embodiment, the outer cover 310 and the outer cover frame 320 are an integral, single structure. The flexible barrel adapter 330 may be composed of a resilient gasket that expands, allowing the microscope objective lens cover 300 to be secured over the objective lens barrel 140. Those skilled in the art are aware of other materials with elastic properties, such as rubber, that may also be used. The flexible barrel adapter 330 may also be secured over the sheet 210 material surrounding the objective lens aperture 220, including the constricting band 230. Similar to the constricting band 230, the diameter of the flexible barrel adapter 330 is typically smaller than the smallest diameter of the lens barrel 140 that is commonly in use and the material used in the flexible barrel adapter 330 will expand to accommodate the largest diameter lens barrel 140 commonly used.

From the above, it is apparent that the present invention provides, for use with a surgical microscope having an objective lens barrel protruding therefrom, drapes, methods of draping the microscope and methods of manufacturing the drapes. In one embodiment, a drape includes: (1) a sheet, having an elastically-deformable objective lens aperture therethrough, that covers at least a portion of the surgical microscope, the objective lens aperture adapted to receive the objective lens barrel therethrough and elastically constrict about the objective lens barrel and (2) a transparent objective lens cover, separate from the sheet and having a flexible barrel adapter, the flexible barrel adapter expandable to fit about and cover the objective lens barrel, the sheet and the objective lens cover cooperating to cover the portion of the surgical microscope, including the objective lens barrel.

Although the present invention and its advantages have been described in detail, those skilled in the art should understand that they can make various changes, substitutions and alterations herein without departing from the spirit and scope of the invention in its broadest form.

What is claimed is:

1. For use with a surgical microscope having an objective lens barrel protruding therefrom, a drape, comprising:
    a sheet, having an elastically-deformable objective lens aperture therethrough, that covers at least a portion of a surgical microscope, said objective lens aperture adapted to receive an objective lens barrel of said surgical microscope therethrough and elastically constrict about said objective lens barrel; and
    a transparent objective lens cover, separate from said sheet and having a flexible barrel adapter, said flexible barrel adapter expandable to fit about and cover said objective lens barrel, said sheet and said objective lens cover cooperating to cover said portion of said surgical microscope, including said objective lens barrel.

2. The drape as recited in claim 1 wherein said objective lens aperture has an elastic band thereabout to render said objective lens aperture elastically deformable.

3. The drape as recited in claim 1 wherein said objective lens aperture forms a particle-resistant seal about said objective lens barrel.

4. The drape as recited in claim 1 wherein said objective lens cover is composed in part of plastic.

5. The drape as recited in claim 1 wherein said flexible barrel adapter comprises a resilient gasket.

6. The drape as recited in claim 1 wherein said flexible barrel adapter fits over said sheet proximate said objective lens aperture.

7. The drape as recited in claim 1 further comprising at least one hook-and-pile fastener, coupled to said sheet, that fixes said sheet to said portion of said surgical microscope.

8. A method of draping a surgical microscope having an objective lens barrel protruding therefrom, comprising the steps of:
    covering at least a portion of said surgical microscope with a sheet having an elastically-deformable objective lens aperture therethrough;
    inserting said objective lens barrel through said objective lens aperture, said objective lens barrel elastically constricting about said objective lens barrel; and
    covering said objective lens barrel with a transparent objective lens cover separate from said sheet and having a flexible barrel adapter, said flexible barrel adapter expandable to fit about said objective lens barrel, said sheet and said objective lens cover cooperating to cover said portion of said surgical microscope, including said objective lens barrel.

9. The method as recited in claim 8 wherein said step of inserting comprises the step of stretching an elastic band about said objective lens aperture.

10. The method as recited in claim 8 further comprising the step of forming a particle-resistant seal about said objective lens barrel.

11. The method as recited in claim 8 wherein said objective lens cover is composed in part of plastic.

12. The method as recited in claim 8 wherein said flexible barrel adapter comprises a resilient gasket.

13. The method as recited in claim 8 wherein said step of covering said objective lens barrel comprises the step of fitting said flexible barrel adapter over said sheet proximate said objective lens aperture.

14. The method as recited in claim 8 further comprising the step of fixing said sheet to said portion of said surgical microscope with at least one hook-and-pile fastener coupled to said sheet.

15. A method of assembling a drape for a surgical microscope having an objective lens barrel protruding therefrom, comprising the steps of:
    creating an elastically-deformable objective lens aperture in a sheet, said sheet adapted to cover at least a portion of said surgical microscope, said objective lens aperture adapted to receive said objective lens barrel therethrough and elastically constrict about said objective lens barrel; and
    forming a transparent objective lens cover, separate from said sheet and having a flexible barrel adapter, said flexible barrel adapter expandable to fit about and cover said objective lens barrel, said sheet and said objective lens cover cooperating to cover said portion of said surgical microscope, including said objective lens barrel.

16. The method as recited in claim 15 wherein said step of creating comprises the step of disposing an elastic band about said objective lens aperture to render said objective lens aperture elastically deformable.

17. The method as recited in claim 15 wherein said objective lens aperture is sized to form a particle-resistant seal about said objective lens barrel.

18. The method as recited in claim 15 wherein said step of forming comprises the step of composing said objective lens cover in part of plastic.

19. The method as recited in claim 15 wherein said step of forming comprises the step of depositing a resilient gasket proximate said flexible barrel adapter.

20. The method as recited in claim 15 wherein said flexible barrel adapter is sized to fit over said sheet proximate said objective lens aperture.

21. The method as recited in claim 15 further comprising the step of coupling at least one hook-and-pile fastener to said sheet, said at least one hook-and-pile fastener allowing said sheet to be fixed to said portion of said surgical microscope.

* * * * *